(12) United States Patent
Puryear et al.

(10) Patent No.: US 11,197,716 B2
(45) Date of Patent: Dec. 14, 2021

(54) MONITORING NERVE ACTIVITY

(71) Applicant: RECOR MEDICAL, INC., Palo Alto, CA (US)

(72) Inventors: Harry A. Puryear, Minnetonka, MN (US); Jin Shimada, Minnetonka, MN (US)

(73) Assignee: RECOR MEDICAL, INC., Palo Alto, CA (US)

(*) Notice: Subject to any disclaimer, the term of this patent is extended or adjusted under 35 U.S.C. 154(b) by 194 days.

(21) Appl. No.: 15/996,978

(22) Filed: Jun. 4, 2018

(65) Prior Publication Data
US 2018/0280082 A1 Oct. 4, 2018

Related U.S. Application Data

(63) Continuation of application No. 15/943,354, filed on Apr. 2, 2018, which is a continuation of application No. 14/683,966, filed on Apr. 10, 2015, now Pat. No. 9,999,463.

(60) Provisional application No. 61/979,339, filed on Apr. 14, 2014.

(51) Int. Cl.
*A61B 5/24* (2021.01)
*A61B 18/14* (2006.01)
*A61B 18/00* (2006.01)

(52) U.S. Cl.
CPC ............ *A61B 18/1492* (2013.01); *A61B 5/24* (2021.01); *A61B 2018/00404* (2013.01); *A61B 2018/00434* (2013.01); *A61B 2018/00505* (2013.01); *A61B 2018/00577* (2013.01); *A61B 2018/00642* (2013.01); *A61B 2018/00702* (2013.01); *A61B 2018/00839* (2013.01)

(58) Field of Classification Search
CPC .............. A61B 5/0004; A61B 5/04001; A61B 18/1492
See application file for complete search history.

(56) References Cited

U.S. PATENT DOCUMENTS

| | | | |
|---|---|---|---|
| 4,709,698 A | 12/1987 | Johnston et al. | |
| 5,657,755 A | 8/1997 | Desai | |
| 6,292,695 B1 | 9/2001 | Webster et al. | |
| 6,837,886 B2 | 1/2005 | Collins et al. | |

(Continued)

OTHER PUBLICATIONS

"U.S. Appl. No. 15/943,354, Non Final Office Action dated Jan. 13, 2020", 6 pgs.

(Continued)

*Primary Examiner* — Michael J D'Abreu
(74) *Attorney, Agent, or Firm* — Vierra Magen Marcus LLP

(57) ABSTRACT

Systems and methods provide interface to a patient's autonomic nerves via an interior lumen wall of a blood vessel. Systems can include a probe having at least one electrode for receiving electrical signals from the interior of the lumen wall. The system can include processing components for extracting the signals from noise within the patient's body. Systems can include stimulation electrodes for providing stimulation and eliciting action potentials within the patient and destructive processes for destroying nervous function. The effect of nerve destruction on the propagation of action potentials can be effectively used as a feedback mechanism for determining the amount of nervous function destruction in the patient.

29 Claims, 8 Drawing Sheets

(56) References Cited

U.S. PATENT DOCUMENTS

| | | | |
|---|---|---|---|
| 7,653,438 B2 | 1/2010 | Deem et al. | |
| 7,722,604 B2 | 5/2010 | Brown et al. | |
| 7,799,021 B2 | 9/2010 | Leung et al. | |
| 8,224,416 B2 | 7/2012 | de la Rama et al. | |
| 8,447,414 B2* | 5/2013 | Johnson | A61N 1/3718 607/63 |
| 8,483,831 B1 | 7/2013 | Hlavka et al. | |
| 8,702,619 B2 | 4/2014 | Wang | |
| 8,876,813 B2 | 11/2014 | Min et al. | |
| 8,909,316 B2 | 12/2014 | Ng | |
| 8,932,289 B2 | 1/2015 | Mayse et al. | |
| 9,014,821 B2 | 4/2015 | Wang | |
| 9,022,948 B2 | 5/2015 | Wang | |
| 9,028,472 B2 | 5/2015 | Mathur et al. | |
| 9,066,720 B2 | 6/2015 | Ballakur et al. | |
| 9,072,902 B2 | 7/2015 | Mathur et al. | |
| 9,155,590 B2 | 10/2015 | Mathur | |
| 9,186,212 B2 | 11/2015 | Nabutovsky et al. | |
| 9,289,132 B2 | 3/2016 | Ghaffari | |
| 9,326,816 B2 | 5/2016 | Srivastava | |
| 9,327,123 B2 | 5/2016 | Yamasaki | |
| 9,333,035 B2 | 5/2016 | Rudie | |
| 9,339,332 B2 | 5/2016 | Srivastava | |
| 9,345,530 B2 | 5/2016 | Ballakur et al. | |
| 9,375,154 B2 | 6/2016 | Wang | |
| 9,427,579 B2 | 8/2016 | Fain et al. | |
| 9,439,598 B2 | 9/2016 | Shimada et al. | |
| 9,649,064 B2 | 5/2017 | Toth et al. | |
| 9,723,998 B2 | 8/2017 | Wang | |
| 9,730,639 B2 | 8/2017 | Toth et al. | |
| 9,743,845 B2 | 8/2017 | Wang | |
| 9,750,560 B2 | 9/2017 | Ballakur et al. | |
| 9,770,291 B2 | 9/2017 | Wang et al. | |
| 9,770,593 B2 | 9/2017 | Gross | |
| 9,801,684 B2 | 10/2017 | Fain et al. | |
| 9,820,811 B2 | 11/2017 | Wang | |
| 9,907,983 B2 | 3/2018 | Thapliyal et al. | |
| 9,931,047 B2 | 4/2018 | Srivastava | |
| 9,956,034 B2 | 5/2018 | Toth et al. | |
| 9,968,790 B2 | 5/2018 | Toth et al. | |
| 9,999,463 B2 | 6/2018 | Puryear et al. | |
| 10,004,458 B2 | 6/2018 | Toth et al. | |
| 10,004,557 B2 | 6/2018 | Gross et al. | |
| 10,010,364 B2 | 7/2018 | Harrington | |
| 10,016,233 B2 | 7/2018 | Pike | |
| 10,022,085 B2 | 7/2018 | Toth et al. | |
| 10,111,708 B2 | 10/2018 | Wang | |
| 10,143,419 B2 | 12/2018 | Toth et al. | |
| 10,179,020 B2 | 1/2019 | Ballakur et al. | |
| 10,179,026 B2 | 1/2019 | Ng | |
| 10,226,633 B2 | 3/2019 | Toth et al. | |
| 10,292,610 B2 | 5/2019 | Srivastava | |
| 10,363,359 B2 | 7/2019 | Toth et al. | |
| 10,368,775 B2 | 8/2019 | Hettrick et al. | |
| 10,376,310 B2 | 8/2019 | Fain et al. | |
| 10,383,685 B2 | 8/2019 | Gross et al. | |
| 10,398,332 B2 | 9/2019 | Min et al. | |
| 10,470,684 B2 | 11/2019 | Toth et al. | |
| 10,478,249 B2 | 11/2019 | Gross et al. | |
| 10,543,037 B2 | 1/2020 | Shah | |
| 2001/0023365 A1 | 9/2001 | Medhkour et al. | |
| 2002/0173724 A1* | 11/2002 | Dorando | A61B 5/0215 600/486 |
| 2003/0074039 A1 | 4/2003 | Puskas | |
| 2004/0097819 A1 | 5/2004 | Duarte | |
| 2004/0122494 A1* | 6/2004 | Eggers | A61F 7/12 607/103 |
| 2005/0159738 A1 | 7/2005 | Visram et al. | |
| 2005/0288730 A1 | 12/2005 | Deem et al. | |
| 2006/0217772 A1* | 9/2006 | Libbus | A61N 1/36057 607/9 |
| 2006/0235286 A1 | 10/2006 | Stone et al. | |
| 2007/0060921 A1 | 3/2007 | Janssen et al. | |
| 2007/0106292 A1 | 5/2007 | Kaplan et al. | |
| 2009/0234407 A1* | 9/2009 | Hastings | A61N 1/3684 607/14 |
| 2009/0248005 A1 | 10/2009 | Rusin et al. | |
| 2012/0232374 A1 | 9/2012 | Werneth et al. | |
| 2012/0265198 A1 | 10/2012 | Crow et al. | |
| 2012/0296232 A1 | 11/2012 | Ng | |
| 2013/0085489 A1 | 4/2013 | Fain et al. | |
| 2013/0096550 A1 | 4/2013 | Hill | |
| 2013/0116737 A1 | 5/2013 | Edwards et al. | |
| 2013/0131743 A1* | 5/2013 | Yamasaki | A61B 5/4041 607/3 |
| 2013/0150749 A1* | 6/2013 | McLean | A61B 5/296 600/546 |
| 2013/0165925 A1 | 6/2013 | Mathur et al. | |
| 2013/0274614 A1 | 10/2013 | Shimada et al. | |
| 2013/0289369 A1 | 10/2013 | Margolis | |
| 2014/0018788 A1* | 1/2014 | Engelman | A61B 18/18 606/33 |
| 2014/0275924 A1* | 9/2014 | Min | A61B 5/24 600/377 |
| 2014/0288551 A1 | 9/2014 | Bharmi et al. | |
| 2014/0288616 A1 | 9/2014 | Rawat et al. | |
| 2015/0289931 A1 | 10/2015 | Puryear et al. | |
| 2016/0000345 A1 | 1/2016 | Kobayashi et al. | |
| 2016/0045121 A1 | 2/2016 | Akingba et al. | |
| 2017/0003531 A1 | 2/2017 | Shimada et al. | |
| 2017/0027460 A1 | 2/2017 | Shimada et al. | |
| 2017/0296264 A1 | 10/2017 | Wang | |
| 2018/0022108 A1 | 1/2018 | Mori et al. | |
| 2018/0042670 A1 | 2/2018 | Wang et al. | |
| 2018/0078307 A1 | 3/2018 | Wang et al. | |
| 2018/0185091 A1 | 7/2018 | Toth et al. | |
| 2018/0221087 A1 | 8/2018 | Puryear et al. | |
| 2018/0249958 A1 | 9/2018 | Toth et al. | |
| 2018/0250054 A1 | 9/2018 | Gross et al. | |
| 2018/0280082 A1 | 10/2018 | Puryear et al. | |
| 2018/0289320 A1 | 10/2018 | Toth et al. | |
| 2018/0310991 A1 | 11/2018 | Pike | |
| 2018/0333204 A1 | 11/2018 | Ng | |
| 2019/0046111 A1 | 2/2019 | Toth et al. | |
| 2019/0046264 A1 | 2/2019 | Toth et al. | |
| 2019/0076191 A1 | 3/2019 | Wang | |
| 2019/0110704 A1 | 4/2019 | Wang | |
| 2019/0134396 A1 | 5/2019 | Toth et al. | |
| 2019/0151670 A1 | 5/2019 | Toth et al. | |
| 2019/0183560 A1 | 6/2019 | Ballakur et al. | |
| 2019/0307361 A1 | 10/2019 | Hettrick et al. | |
| 2020/0046248 A1 | 2/2020 | Toth et al. | |
| 2020/0077907 A1 | 3/2020 | Shimada et al. | |

OTHER PUBLICATIONS

"U.S. Appl. No. 15/943,354, Response filed Dec. 19, 2019 to Restriction Requirement dated Nov. 20, 2019", 8 pgs.

"U.S. Appl. No. 15/943,354, Restriction Requirement dated Nov. 20, 2019", 8 pgs.

"U.S. Appl. No. 14/683,966, 312 Amendment filed Mar. 13, 2018", 10 pgs.

"U.S. Appl. No. 14/683,966, Corrected Notice of Allowance dated May 22, 2018", 4 pgs.

"U.S. Appl. No. 14/683,966, Non Final Office Action dated Jun. 12, 2017", 14 pgs.

"U.S. Appl. No. 14/683,966, Notice of Allowance dated Jan. 31, 2018", 8 pgs.

"U.S. Appl. No. 14/683,966, PTO Response to Rule 312 Communication dated Mar. 29, 2018", 2 pgs.

"U.S. Appl. No. 14/683,966, Response filed Nov. 10, 2017 to Non Final Office Action dated Jun. 12, 2017", 13 pgs.

"U.S. Appl. No. 15/204,349, Preliminary Amendment filed Nov. 30, 2016", 3 pgs.

"U.S. Appl. No. 15/204,349, Restriction Requirement dated May 17, 2018", 7 pgs.

"U.S. Appl. No. 15/943,354, Preliminary Amendment filed Apr. 3, 2018", 9 pgs.

Accornero, Neri, et al., "Selective Activation of Peripheral Nerve Fibre Groups of Different Diameter by Triangular Shaped Stimulus Pulses", J. Physiol. (1977), 273, pp. 539-560.

(56) References Cited

OTHER PUBLICATIONS

Papademetriou, et al., "Renal Sympathetic Denervation: Hibernation or Resurrection?", Cardiology 2016; 135, 11 pgs.
"U.S. Appl. No. 15/299,694, Restriction Requirement dated Aug. 6, 2018", 6 pgs.
"U.S. Appl. No. 15/299,694, Response filed Oct. 8, 2018 to Restriction Requirement dated Aug. 6, 2018", 7 pgs.
"U.S. Appl. No. 15/299,694, Non Final Office Action dated Nov. 27, 2018", 15 pgs.
"U.S. Appl. No. 15/299,694, Response filed Feb. 27, 2019 to Non Final Office Action dated Nov. 27, 2018", 10 pgs.
"U.S. Appl. No. 15/204,349, Final Office Action dated Apr. 22, 2019", 16 pgs.
"U.S. Appl. No. 15/299,694, Final Office Action dated Apr. 22, 2019", 16 pgs.
"U.S. Appl. No. 15/204,349, Response filed Jun. 24, 2019 to Final Office Action dated Apr. 22, 2019", 12 pgs.
"U.S. Appl. No. 15/299,694, Response filed Jun. 24, 2019 to Final Office Action dated Apr. 22, 2019", 11 pgs.
"U.S. Appl. No. 15/204,349, Advisory Action dated Jul. 9, 2019", 5 pgs.
"U.S. Appl. No. 15/299,694, Advisory Action dated Jul. 9, 2019", 5 pgs.
"U.S. Appl. No. 16/517,180, Preliminary Amendment filed Jul. 19, 2019", 12 pgs.
"U.S. Appl. No. 15/204,349, Non Final Office Action dated Nov. 27, 2018", 14 pgs.
"U.S. Appl. No. 15/204,349, Response filed Feb. 27, 2019 to Non Final Office Action dated Nov. 27, 2018", 10 pgs.
"U.S. Appl. No. 15/204,349, Response filed Jun. 5, 2018 to Restriction Requirement dated May 17, 2018", 7 pgs.
"U.S. Appl. No. 15/943,354, Response filed Jul. 20, 2020 to Non Final Office Action dated Apr. 20, 2020", 15 pgs.
"U.S. Appl. No. 15/943,354, Non Final Office Action dated Apr. 20, 2020", 7 pgs.
Final Office Action dated Dec. 10, 2020, U.S. Appl. No. 15/943,354, filed Apr. 2, 2018.
Response to Final Office Action dated Jan. 22, 2021, U.S. Appl. No. 15/943,354, filed Apr. 2, 2018.
A. Diedrich et al., Analysis of Raw Microneurographic Recordings Based on Wavelet De-Noising Technique and Classification Algorithm: Wavelet Analysis in Microneurography, IEEE Trans Biomed Eng. Jan. 2003 ; 50(1): 41-50. doi:10.1109/TBME.2002.807323.
J. Carter, Microneurography and Sympathetic Nerve Activity: A Decade-By-Decade Journey across 50 Years, Journal of Neurophysiology, vol. 121, No. 4. doi:10.1152/jn.00570.2018.
R. R. Harrison et al., A Low-Power Integrated Circuit for a Wireless 100-Electrode Neural Recording System, IEEE Journal of Solid-State Circuits, vol. 42, No. 1, pp. 123-133, Jan. 2007. doi: 10.1109/JSSC.2006.886567.

G.K.K. Nair et al., The Need for and the Challenges of Measuring Renal Sympathetic Nerve Activity, Heart Rhythm 2016; 13:1166-1171.
R. Olsson and K. Wise, A Three-Dimensional Neural Recording Microsystem With Implantable Data Compression Circuitry, ISSCC. 2005 IEEE International Digest of Technical Papers. Solid-State Circuits Conference, 2005., San Francisco, CA, 2005, pp. 558-559 Vol. 1. doi:10.1109/JSSC.2005.858479.
J. Osborn, Catheter-Based Renal Nerve Ablation as a Novel Hypertension Therapy, Lost, and Then Found, in Translation.
A. Salmanpour, L. J. Brown and J. K. Shoemaker, Detection of Single Action Potential in Multi-Unit Postganglionic Sympathetic Nerve Recordings in Humans: A Matched Wavelet Approach, 2010 IEEE International Conference on Acoustics, Speech and Signal Processing, Dallas, TX, 2010, pp. 554-557. doi: 10.1109/ICASSP.2010.5495604.
M. P. Schlaich et al., Renal Denervation: A Potential New Treatment Modality for Polycystic Ovary Syndrome?, Journal of Hypertension, vol. 29, No. 5, pp. 991-996 2011. doi:10.1097/HJH.0b013e328344db3a.
J. Tank et al., Spike Rate of Multi-Unit Muscle Sympathetic Nerve Fibers Following Catheter-Based Renal Nerve Ablation, J Am. Soc Hypertens, Oct. 2015 ; 9(10): 794-801. doi:10.1016/j.jash.2015.07.012.
J. Xu et al, A Bidirectional Neuromodulation Technology for Nerve Recording and Stimulation, Micromachines, vol. 9,11 538. Oct. 23, 2018. doi:10.3390/mi9110538.
J. Xu, T. Wu and Z. Yang, A New System Architecture for Future Long-Term High-Density Neural Recording, IEEE Transactions on Circuits and Systems II: Express Briefs, vol. 60, No. 7, pp. 402-406, Jul. 2013. doi:10.1109/TCSII.2013.2258270.
N. Ivanisevic, "Circuit Design Techniques for Implantable Closed-Loop Neural Interfaces," Doctoral Thesis in Information and Communication Technology, KTH School of Electrical Engineering and Computer Science, Sweden, May 2019, 92 pages.
H. Heffner et al., "Gain, Band Width, and Noise Characteristics of the Variable-Parameter Amplifier," Journal of Applied Physics, vol. 29, No. 9, Sep. 1958, 11 pages.
P. Maslov, "Recruitment Pattern of Muscle Sympathetic Nerve Activity in Chronic Stable Heart Failure Patients and in Healthy Control Subjects," Doctoral Dissertation, University of Split, Croatia, 2013, 68 pages.
M.B.I. Reaz et al., "Techniques of EMG signal analysis: detection, processing, classification and applications," Biological Procedures Online, Jan. 2006, 25 pages.
Advisory Action dated Feb. 19, 2021, U.S. Appl. No. 15/943,354, filed Apr. 2, 2018.
Non-final Office Action dated Apr. 15, 2021, U.S. Appl. No. 15/943,354, filed Apr. 2, 2018.
Response to Office Action dated Jun. 22, 2021, U.S. Appl. No. 15/943,354, filed Apr. 2, 2018.

* cited by examiner

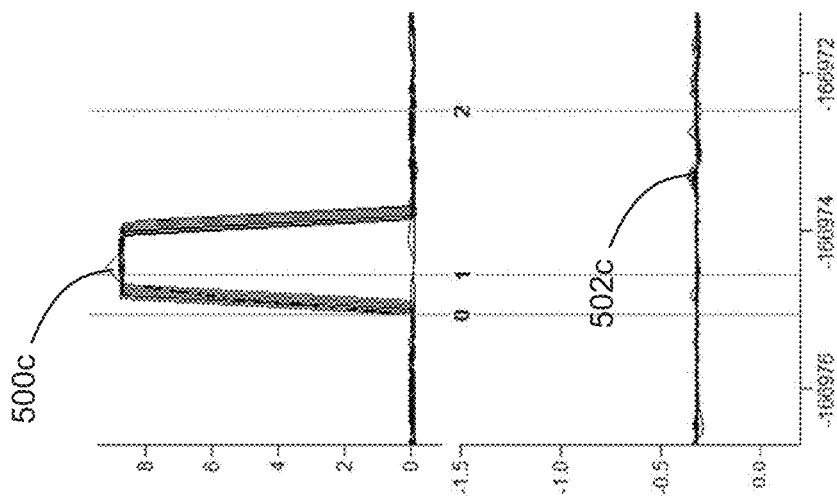
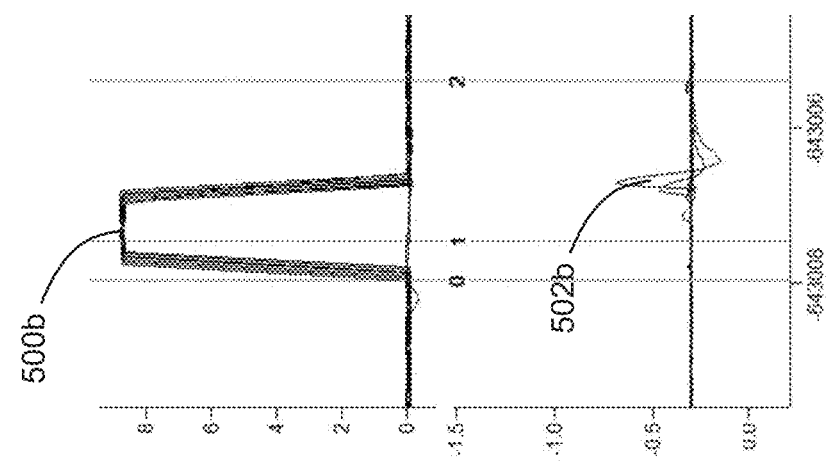
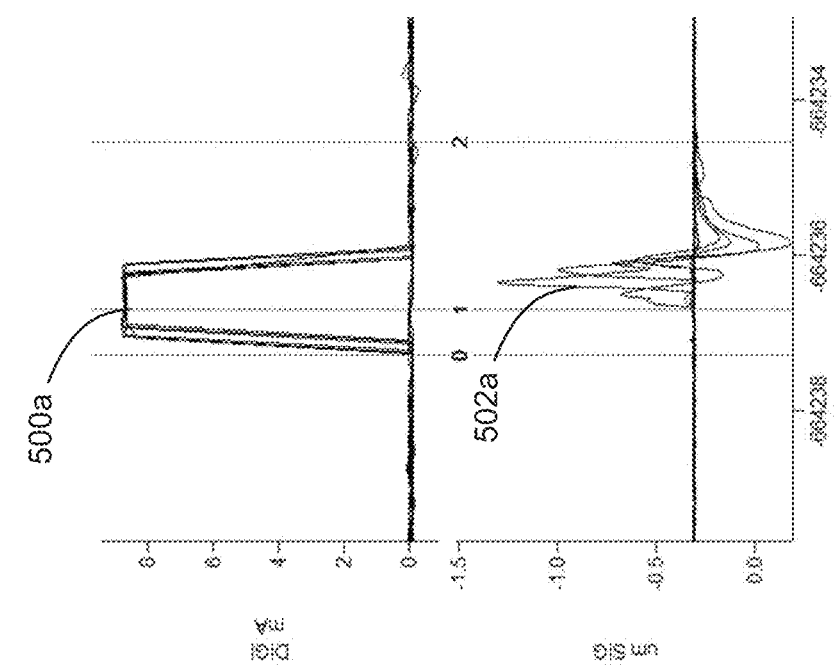

MONITORING NERVE ACTIVITY

CLAIM OF PRIORITY

This application is a continuation of and claims priority to U.S. patent application Ser. No. 15/943,354, filed Apr. 2, 2018, which is a continuation of and claims priority to U.S. patent application Ser. No. 14/683,966, filed Apr. 10, 2015, and issued on Jun. 19, 2018 as U.S. Pat. No. 9,999,463, which claims the benefit of priority to U.S. Provisional Application Ser. No. 61/979,339, filed Apr. 14, 2014. The contents of the above applications are incorporated herein by reference in their entireties.

BACKGROUND

New medical therapies have been practiced whereby a probe such as a needle, catheter, wire, etc. is inserted into the body to a specified anatomical location and destructive means are conveyed to nerves by means of the probe to irreversibly damage tissue in the nearby regions. The objective is to abolish nerve function in the specified anatomic location. The result is that abnormally functioning physiological processes can be terminated or modulated back into a normal range. Unfortunately such medical therapies are not always successful because there is no means to assess that the nervous activity has been successfully abolished.

An example is renal nerve ablation to relieve hypertension. Various studies have confirmed the relationship of renal nerve integrity with blood pressure regulation. In various renal ablation procedures, a catheter is introduced into a hypertensive patient's arterial vascular system and advanced into the renal artery. Renal nerves are located in the arterial wall and in regions adjacent to the artery. Destructive means are delivered to the renal artery wall to an extent intended to cause destruction of nerve activity. Destructive means include energy such as RF, ultrasound, laser or chemical agents. The objective is to abolish the renal sympathetic nerve activity. Such nerve activity is an important factor in the creation of hypertension and abolishment of the nerve activity reduces hypertension.

Unfortunately not all patients respond to this therapy. Renal nerve ablation procedures are often ineffective, and are caused by a poor probe/tissue interface. Accordingly, insufficient quantities of destructive means are delivered to the sympathetic nerve fibers transmitting along the renal artery. One reason is that the delivery of destructive means to the arterial wall does not have a feedback control mechanism to assess the destruction of the nerve activity. As a consequence an insufficient quantity of destructive means is delivered and nervous activity is not abolished. Clinicians therefore, require a means of improving the probe/tissue interface, and a technology to monitor the integrity of the nerve fibers passing through the arterial wall in order to confirm destruction of nerve activity prior to terminating therapy. Current technology for the destruction of sympathetic nerve activity does not provide practitioners with a feedback control mechanisms to detect when the desired nervous activity destruction is accomplished. Nerve destructive means are applied empirically without knowledge that the desired effect has been achieved.

It is known that ablation of the renal artery, with sufficient energy, is able to effect a reduction in both systolic and diastolic blood pressure. Current methods are said to be, from an engineering perspective, open loop; i.e., the methods used to effect renal denervation do not employ any way of measuring, in an acute clinical setting, the results of applied ablation energies. It is only after application of such energies and a period of time (3-12 months) that the effects of the procedure are known.

The two major components of the autonomic nervous system (ANS) are the sympathetic and the parasympathetic nerves. The standard means for monitoring autonomic nerve activity is situations such as described is to insert very small electrodes into the nerve body or adjacent to it. The nerve activity creates an electrical signal in the electrodes which is communicated to a monitoring means such that a clinician can assess nerve activity. This practice is called microneurography and its practical application is by inserting the electrodes transcutaneously to the desired anatomical location. This is not possible in the case of the ablation of many autonomic nerves proximate arteries, such as the renal artery, because the arteries and nerves are located within the abdomen and cannot be accessed transcutaneously with any reliability. Thus the autonomic nerve activity cannot be assessed in a practical or efficacious manner.

The autonomic nervous system is responsible for regulating the physiological processes of circulation, digestion, metabolism, reproduction, and respiration among others. The sympathetic nerves and parasympathetic nerves most often accompany the blood vessels supplying the body organs which they regulate. Examples of such include but are not limited to the following: (1) Nerves regulating liver function accompany the hepatic artery and the portal vein. (2) Nerves regulating the stomach accompany the gastroduodenal, the right gastroepiploic artery, and the left gastric artery. (3) Nerves regulating the spleen accompany the lineal artery. (4) Nerves from the superior mesenteric plexus accompany the superior mesenteric artery, where both the artery and the nerves branch to the pancreas, small intestine, and large intestine. (5) Nerves of the inferior mesenteric plexus accompany the inferior mesenteric artery and branch with the artery to supply the large intestine, the colon, and the rectum.

When monitoring ANS activity, one must generally differentiate between the electrical signals generated by the ANS and those generated by muscle activity, which is commonly called EMG. EMG signals possess amplitudes several orders of magnitude larger than compared to those of the ANS. Probes possessing electrodes have been used to assess the EMG of the heart, stomach, intestines, and other muscles of the body. Such probes and their means and methods for detecting and analyzing the electric signals are not suitable for use with signals generated by the ANS.

Deficiencies in the use of existing therapeutic protocols in denervation of autonomic nerves proximate arteries include: 1. The inability to determine the appropriate lesion sites along the artery that correspond to the track of nerves; 2. The inability to verify that the destructive devices are appropriately positioned on the arterial wall, normalizing the tissue/device interface and enabling energy transfer through the vessel wall, and 3. Inability to provide feedback to the clinician intraoperatively to describe lesion completeness or the integrity of the affected nerve fibers. As a consequence, current autonomic nerve ablation procedures are performed in a 'blinded' fashion; the clinician performing the procedure does not know where the nerves are located; and further, whether the nerves have truly been ablated. Instead, surrogates such as catecholamine spillover into the circulating blood have been used to attempt to evaluate the termination of autonomic nerve activity such as renal sympathetic nerve activity (RSNA). It is entirely likely that this deficiency could largely be responsible for the current questionable data coming from clinical trials in the US. Therefore, a system designed to indicate with precision, and in real time, whether ablation was successful is urgently needed.

SUMMARY

Aspects of the disclosure are generally toward systems and methods for interfacing with the autonomic nervous system of a patient via an interior wall of a blood vessel. In some embodiments, a system includes a probe having at least one electrode capable of detecting electrical signals from an interior wall of a blood vessel. The system can include an electrical control unit (ECU) in electrical communication with the probe and capable of receiving an electrical signal from the at least one electrode of the probe. The ECU can process the received signal to product an output signal, and present information including information about the output signal, the received signal, or processing information. Such systems can be used, for example, in diagnostic procedures for assessing the status of a patient's nervous activity proximate the blood vessel.

In some examples, the system can include a stimulation electrode for providing an electrical stimulus into the interior wall of the blood vessel. The electrical stimulus can be sufficient to provoke an elicited potential in the patient's nerves. The system can receive and process a signal including the elicited potential. Embodiments of the system can further perform a nerve destruction process to destroy nervous tissue or function proximate the blood vessel. The system can evoke and detect elicited potentials before and after the nerve destruction process and compare the detected potentials to determine the effective amount of destruction that has taken place.

In further examples, nerve destruction processes can be performed after at least one diagnostic procedure. For example, a diagnostic procedure can be performed to determine the level of nervous activity in nerves proximate a patient's blood vessel. The level of activity can be analyzed to determine whether or not a nerve destruction process is likely to be effective therapy for a patient. If so, nerve destruction processes can be performed.

BRIEF DESCRIPTION OF THE DRAWINGS

FIG. 5A-5C are a series of exemplary plots showing the effect of nerve destruction on elicited potentials in a patient's nervous system.

DETAILED DESCRIPTION

Figure 1A:
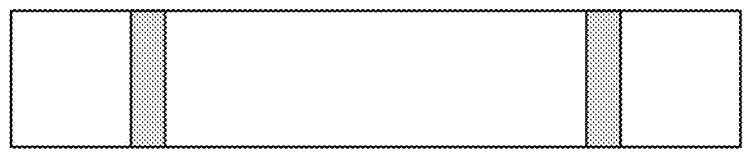
FIGS. 1A-1D are exemplary probe designs according to various embodiments.

The following detailed description is exemplary in nature and is not intended to limit the scope, applicability, or configuration of the invention in any way. Rather, the following description provides some practical illustrations for implementing various embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives. Some such alternatives or variations may be more fully appreciated with regard to U.S. patent application Ser. No. 13/796,944, filed on Mar. 12, 2013, now granted as U.S. Pat. No. 9,439,598, which is hereby incorporated by reference in its entirety.

This invention enables the real-time assessment of sympathetic and parasympathetic nerve activity by comparing stimulus-elicited potentials before and after the delivery of a destructive means to the selected nerves. Electrical stimulation is delivered to the arterial wall in a fashion to reliably elicit maximal nerve activity. The resultant activity transmits distally past a destructive means and towards a system used to record the elicited activity. Comparisons of the neural bursts elicited before and after ablation can be used to indicate the continuity and integrity of the interposed nerve fibers.

Various methods of eliciting and assessing autonomic nerve activity can include inserting a probe containing both therapeutic means for performing destructive processes and stimulating and recording electrodes for eliciting and assessing nervous activity into the patient's body to a desired anatomic location. In some examples, the probe can be inserted through a blood vessel of the patient in order to elicit and assess nerve activity associated with nerves proximate that blood vessel. In still further embodiments, the probe is inserted into an artery into an organ, for example, those described above.

In some embodiments, a clinician may first use the electrodes in a monitoring fashion to establish baseline nervous system function. Alternatively, the clinician may first use the electrodes in a stimulation mode to initiate a nervous activity response which can be measured by the electrodes in a monitoring mode. The clinician may then apply destructive means to the tissue, such as described in U.S. patent application Ser. No. 13/796,944, now granted as U.S. Pat. No. 9,439,598. The clinician may next apply the cycle of nerve stimulation and monitoring to assess whether or not the nerve activity has been abolished. If nervous activity still exists, then the device may indicate to the clinician a value indicative of nerve destruction completeness. For example, the device may estimate an amount of nerve destruction based on the magnitude of detected nervous activity compared to the magnitude of detected nervous activity prior to nerve destruction. The estimated amount of nerve destruction may be in the form of a percentage, for example. At this time, the clinician may assess the level of denervation or destruction and stop, or proceed to deliver another application of destructive means for a more complete lesion. The cycle of application, stimulation, and monitoring may be repeated until nervous activity is abolished, and/or the clinician has reached an intended level of denervation.

Various systems and devices can be used for performing such processes. Some embodiments of the invention comprise a probe for inserting into the patient, for example into a patients renal artery or any other appropriate lumen in the patients vasculature. The probe can include a plurality of electrodes directing an electrical stimulus into the patient's body, and for detecting electrical signals elicited within the patient. In various embodiments, electrodes can be arranged along the axis of the probe, around the circumference of the probe, or in any other appropriate arrangement for carrying out various methods according to the present invention. Various electrode configurations are described in U.S. patent application Ser. No. 13/796,944, now granted as U.S. Pat. No. 9,439,598. In some configurations, the probe and electrodes are such that, when the probe is inserted into a patent's artery, the electrodes are placed in contact with the artery lumen wall. Such contact permits the application of electrical stimulation from the electrodes to the wall, and the detection of electrical signals from the wall via the electrodes. Various exemplary electrode configurations including a varying number of electrodes are shown in FIGS. 1A-1D and described below.

In some embodiments, such as that shown in FIG. 1A, the probe comprises a first electrode and a second electrode. Such a system can further include a third electrode applied on the patient's skin (not shown). A first electrode mounted on the probe can be used to deliver an electrical stimulus to the surrounding tissue in a monopolar fashion, with the electrode placed on the person's skin being used as the return electrode during stimulation. Distal to the stimulating electrode, the second electrode can be used to record elicited bursts of autonomic activity resulting from the stimulus from the first electrode to the third electrode. In some embodiments, during a recording session, the electrode placed on the skin can be used as the indifferent electrode of the electrode pair.

Figure 1B:
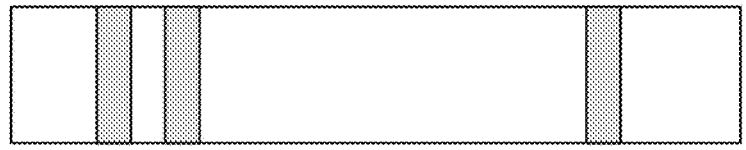

An alternate configuration, such as is shown in FIG. 1B, can include three electrodes on the probe. In such a configuration two electrodes would be dedicated to stimulation and the third would be paired with the external electrode for monitoring.

Figure 1C:
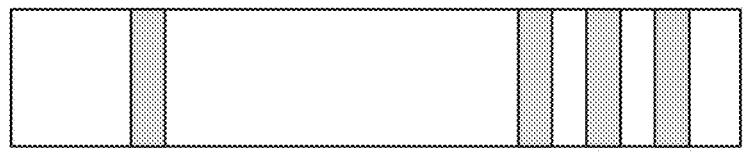

Another alternative configuration, shown in FIG. 1C, can include 4 electrodes on a single probe: one stimulating electrode, and three recording electrodes. The three recording electrodes can be setup to include an active electrode, an inactive electrode and a common electrode, for example. The one stimulating electrode can operate in a monopolar fashion, wherein an external surface electrode positioned on the patient's skin can serve as a return electrode. Alternatively, two electrodes on the probe can be used as stimulating electrodes and can operate in a bipolar fashion, while the remaining two electrodes could be used for recording/detecting signals, such as in the form of an active and inactive pair.

Figure 1D:

Still another alternative configuration, such as is shown in FIG. 1D, can include 5 electrodes on a single probe: two stimulating electrodes to deliver stimulation in a bipolar fashion, and three recording electrodes, for example active, inactive and common electrodes. In general, any number of electrodes can be used for any number of purposes, such as delivering stimulation in a monopolar or bipolar fashion, recording/detecting electrical signals, or measuring any other electrical parameter that might be desired (e.g., resistance, capacitance, etc.). In various embodiments, properties of the recording electrodes can be adjusted to best receive action potentials or other signals passing along the arterial wall. For instance, in some examples, the impedance, separation distance, and size and geometry of the recording electrodes can be adjusted.

It will be appreciated that, while various examples are shown in FIGS. A-1D, suitable probes can include any number of electrodes for performing a variety of functions. For instance, further embodiments of a probe can include three or more stimulating electrodes. In some such examples, stimulating electrodes can include a pair of electrodes for bipolar stimulation as well as a reference electrode or a blocking electrode, as will be described below. In other embodiments, additional electrodes (e.g., third electrode, fourth electrode, etc.) can be can be used as alternative electrodes in the event that a first pair of electrodes does not make adequate electrical contact with the arterial wall of the patient. In such embodiments, alternate stimulating electrodes can be used to provide unipolar or bipolar stimulation to the patient's arterial wall.

In some embodiments, means for applying destructive energy to nerves within or proximate the probe are provided. Such destructive means can include, for example, radiofrequency (RF), ultrasonic, microwave, laser or chemical agents. In some embodiments, the destructive means are applied between the stimulating electrode(s) and the recording electrode(s). Accordingly, the stimulating electrode(s) applies a stimulus to the arterial wall and elicits a potential within the patient that travels at some propagation velocity (e.g., between approximately 0.2 m/s and approximately 8 m/s) toward the recording electrode(s), where it can be detected. When a destructive process is performed between the stimulating and recording electrode(s), subsequent elicited potentials traveling from proximate the stimulating electrode(s) toward the recording electrode(s) must traverse the region of nerves to which destructive means has been applied. Accordingly, any effect that the destruction process has on the elicited potential can be observed at the recording electrode(s).

Figure 2:
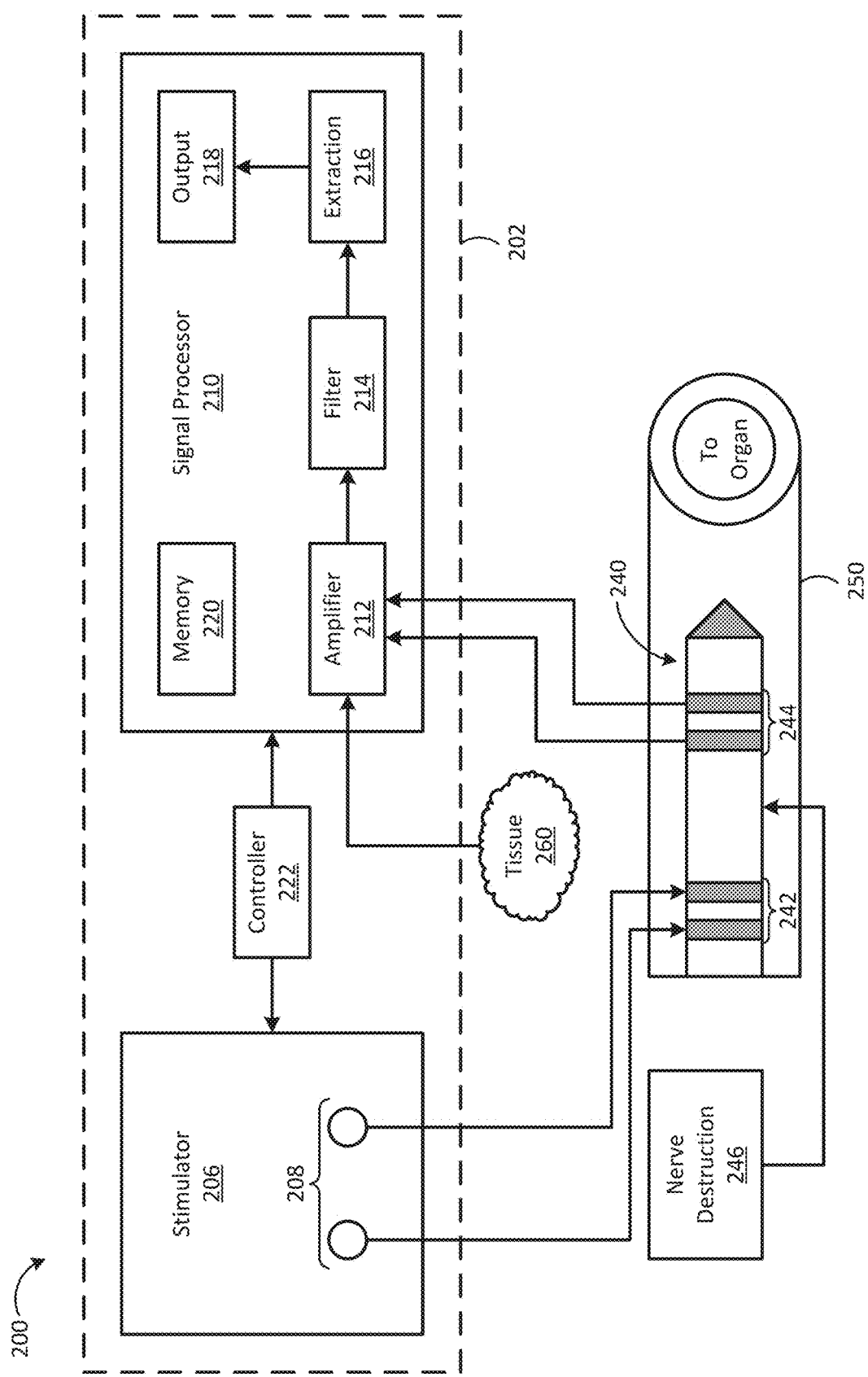
FIG. 2 is a schematic diagram of an exemplary system for interfacing with a patient's arterial nerves.

As shown in FIGS. 1A-1D, the stimulating electrodes are shown on the left side of the probe, while the recording electrodes are shown on the right side. In some embodiments, the probe is inserted into an artery such that the recording electrodes are more proximate an organ associated with the artery than are the stimulating electrodes, such as shown in FIG. 2. However, in alternative embodiments, the stimulating electrodes can be more proximate the organ than the recording electrodes.

Any number of electrodes on the probe can generally be in electrical communication with electrical circuitry for applying electrical signals (e.g., stimulation signals) stimulating electrodes or for receiving and/or processing signals from the electrodes. In some examples, circuitry can include various components, such as a processor and operational amplifier with capacitance control in electrical communication with an active recording electrode on the probe for processing received electrical signals. In some embodiments, the active electrode can possess high impedance. Additionally or alternatively, the active electrode can be a part of an active electrode circuit (e.g., an active electrode in communication with circuitry such as amplifier, processor, etc.), which can itself be configured to have a high input impedance. This design can block electrical noise generated by the various sources inherent to the intravascular space, such as blood flow or vascular muscular contraction from being amplified. In addition, such circuitry can limit the detection of nerve firing to a selective region within the vessel's wall. In some configurations, the amount of impedance and applied electrical signal can be dependent on the size and number of recording electrodes, as the interference effects are proportional to the total surface area of the electrode(s) used. In various embodiments, impedance loading can be positioned prior to an amplifier or can be incorporated into the amplifier design.

In some embodiments, the probe and electrical circuitry can be a part of a system for stimulating, monitoring, and destructing nervous tissue. In some such systems, the electrical circuitry can be a part of or otherwise in electrical communication with an electronic control unit (ECU). In various embodiments, the ECU can include a signal emitting portion and/or a signal receiving portions, and can be configured to emit electrical signals to and/or to receive electrical signals from the probe, respectively.

FIG. 2 is a system diagram of an exemplary system for interfacing with a patient's arterial nerves. As shown, the system 200 of FIG. 2 includes an ECU 202 in electrical communication with a probe 240 inserted in an artery 250 of a patient. The ECU 202 includes a stimulator 206 having electrodes 208 in electrical communication with stimulating electrodes 242 on the probe 240. The stimulator 206 can emit electrical signals to the stimulating electrodes 242 via electrodes 208. When emitting a signal to the probe, the signal can have specific voltage, amperage, duration, and/or frequency of application that will cause nerve cell activation. In an exemplary embodiment, the electrodes 208 can include an anode and a cathode. Further, in some such embodiments, the cathode can be electrically coupled to a stimulating electrode 242 that is located distally from a stimulating electrode 242 that is electrically coupled to the anode. It will be appreciated that, in such an example, stimulating electrodes 242 can similarly be referred to as the anode and cathode due to the respective electrical connection between stimulating electrodes 242 and electrodes 208. That is, electrodes 242 may include an anode and a cathode based on functional operation associated with respectively connected electrodes 208. Thus, in some examples, the probe 240 includes an anode and a cathode for applying a stimulation signal to the arterial wall. In some such examples, the cathode can be located distally with respect to the anode.

Upon receiving the signal, the stimulating electrodes of the probe can apply electrical energy to a patient's nerves through the arterial wall based on the received signal. The stimulus can have any of a variety of known waveforms, such as a sinusoid, a square wave form or a triangular wave form, as taught, for example, in the paper "Selective activation of peripheral nerve fiber groups of different diameter by triangular shaped stimulus pulses," by Accornero (Journal of Physiology. 1977 December; 273(3): 539-560). In various examples, the stimulation can be applied for durations between approximately 0.05 ms and approximately 2 ms. Such signals can be applied through a single, unipolar electrode or a bipolar electrode, for example, as described with regard to the various probe configurations of FIGS. 1A-1D. In some examples, stimulation signals can be applied via a bipolar electrode with "anodal blocking," as will be described below.

The probe 240 includes recording electrodes 244, in the illustrated embodiment positioned distally from stimulating electrodes 242. The recording electrodes 244 can be configured to detect electrical signals in the patient's nerves at a location separate from the stimulating electrodes 242. For example, the recording electrodes 244 can be used to detect an elicited potential caused by a stimulus from the stimulating electrodes 242 and propagating toward the organ.

In some configurations, the stimulation of nerves to evoke an elicited potential can cause such a potential to propagate in every direction along the nerve fibers. In some situations, it can be undesirable for such a potential to propagate unnecessarily through the nerve for patient safety and/or desired signal isolation purposes. In some configurations, the propagation of elicited action potentials can be "blocked" by applying an electrical signal to a portion of the nerve. Accordingly, in some embodiments, a probe or additional component can include electrodes configured to reduce or eliminate an elicited potential from propagating undesirably. For example, with reference to FIG. 2, the probe 240 can include a third stimulating electrode (not shown) further from the organ along the arterial wall than the first and second stimulating electrodes 242. During the application of a stimulation signal, a blocking stimulation pulse can be applied via the third electrode to prevent elicited action potentials from travelling proximally along the patient's nerves while permitting the action potential to propagate toward the recording electrodes 244.

In some embodiments, the ECU 202 can digitally sample the signal on the recording electrode(s) 244 to receive the electrical signal from the probe 240. In alternate embodiments, the signal can be recorded as an analog signal. When receiving an electrical signal from the probe 240, the ECU 202 can perform filtering and/or other processing steps on the signal. Generally, such steps can be performed to discriminate the signal from the probe from any background noise within the patient's vasculature such that the resulting output is predominantly the signal from nerve cell activation. In some instances, the ECU 202 can modulate the electrical impedance of the signal receiving portion in order to accommodate the electrical properties and spatial separation of the electrodes mounted on the probe in a manner to achieve the highest fidelity, selectively and resolution for the signal received. For example, electrode size, separation, and conductivity properties can impact the field strength at the electrode/tissue interface.

Additionally or alternatively, the ECU 202 can comprise a headstage and/or an amplifier to perform any of offsetting, filtering, and/or amplifying the signal received from the probe. In some examples, a headstage applies a DC offset to the signal and performs a filtering step. In some such systems, the filtering can comprise applying notch and/or band-pass filters to suppress particular undesired signals having a particular frequency content or to let pass desired signals having a particular frequency content. An amplifier can be used to amplify the entire signal uniformly or can be used to amplify certain portions of the signal more than others. For example, in some configurations, the amplifier can be configured to provide an adjustable capacitance of the recording electrode, changing the frequency dependence of signal pick-up and amplification. In some embodiments, properties of the amplifier, such as capacitance, can be adjusted to change amplification properties, such as the resonant frequency, of the amplifier.

In the illustrated embodiment of FIG. 2, the ECU 202 includes an amplifier 212 in communication with the recording electrodes 244 of the probe 240 in order to receive electrical signals therefrom. The amplifier 212 can include any appropriate amplifier for amplifying desired signals or attenuating undesired signals. In some examples, the amplifier has a high common-mode rejection ratio (CMRR) for eliminating or substantially attenuating undesired signals present in each at each of the recording electrodes 244. In the illustrated embodiment, the amplifier 212 is electrically coupled to tissue 260 of the patient for providing a reference signal to the amplifier. In some embodiments, amplifier 212 can be adjusted as described above, for example, via an adjustable capacitance or other attributes of the amplifier.

In the exemplary system 200 of FIG. 2, the ECU 202 further includes a filter 214 for enhancing the desired signal in the signal received from recording electrodes 244. As described, the filter 214 can include a band-pass filter, a notch filter, or any other appropriate filter to isolate desired signals from the received signals. Similar to the amplifier 212 discussed above, in some embodiments, various properties of the filter 214 can be adjusted to manipulate its filtering characteristics. For example, the filter may include an adjustable capacitance or other parameter to adjust its frequency response.

At least one of amplification and filtering of the signal received at the recording electrodes 244 can allow for extraction of the desired signal at 216. In some embodiments, extraction 216 comprises at least one additional processing step to isolate desired signals from the signal received at recording electrodes 244, such as preparing the signal for output at 218. In some embodiments, the functionalities of any combination of amplifier 212, filter 214, and extraction 216 may be combined into a single entity. For instance, the amplifier 212 may act to filter undesired frequency content from the signal without requiring additional filtering at a separate filter.

In some embodiments, the ECU 202 can record emitted stimuli and/or received signals. Such data can be subsequently stored in permanent or temporary memory 220. The ECU 202 can comprise such memory 220 or can otherwise be in communication with external memory (not shown). Thus, the ECU 202 can be configured to emit stimulus pulses to electrodes of the probe, record such pulses in a memory, receive signals from the probe, and also record such received signal data. While shown in FIG. 2 as being a part of the processor, it will be appreciated that the memory in or associated with the ECU 202 can be internal or external to any part of the ECU 202 or the ECU 202 itself.

The ECU 202 or separate external processor can further perform calculations on the stored data to determine characteristics of signals either emitted or received via the probe. For example, in various embodiments, the ECU 202 can determine any of the amplitude, duration, or timing of occurrence of the received or emitted signals. The ECU 202 can further determine the relationship between the received signal and the emitted stimulus signal, such as a temporal relationship therebetween. In some embodiments, the ECU 202 performs signal averaging on the signal data received from the probe. Such averaging can act to reduce random temporal noise in the data while strengthening the data corresponding to any elicited potentials received by the probe. An exemplary data collection procedure is outlined below:

1. Generate a stimulus pulse
2. Sample or record data from the receiving over a time period of interest; stop sampling or recording after period of interest (e.g., after any elicited potential might be detected)
3. Repeat steps 1 and 2; add the resulting samples to those already sampled
4. Repeat steps 1 through 3 as needed Averaging as such can result in a signal in which temporally random noise is generally averaged out and the signal present in each recorded data set, such as elicited potentials, will remain high. In some embodiments, each iteration of the process can include a synchronization step so that each acquired data set can be temporally registered to facilitate averaging the data. That is, events that occur consistently at the same time during each iteration may be detected, while temporally random artifacts (e.g., noise) can be reduced. In general, the signal to noise ratio resulting in such averaging will improve by the square root of the number of samples averaged in order to create the averaged data set.

Figure 4:
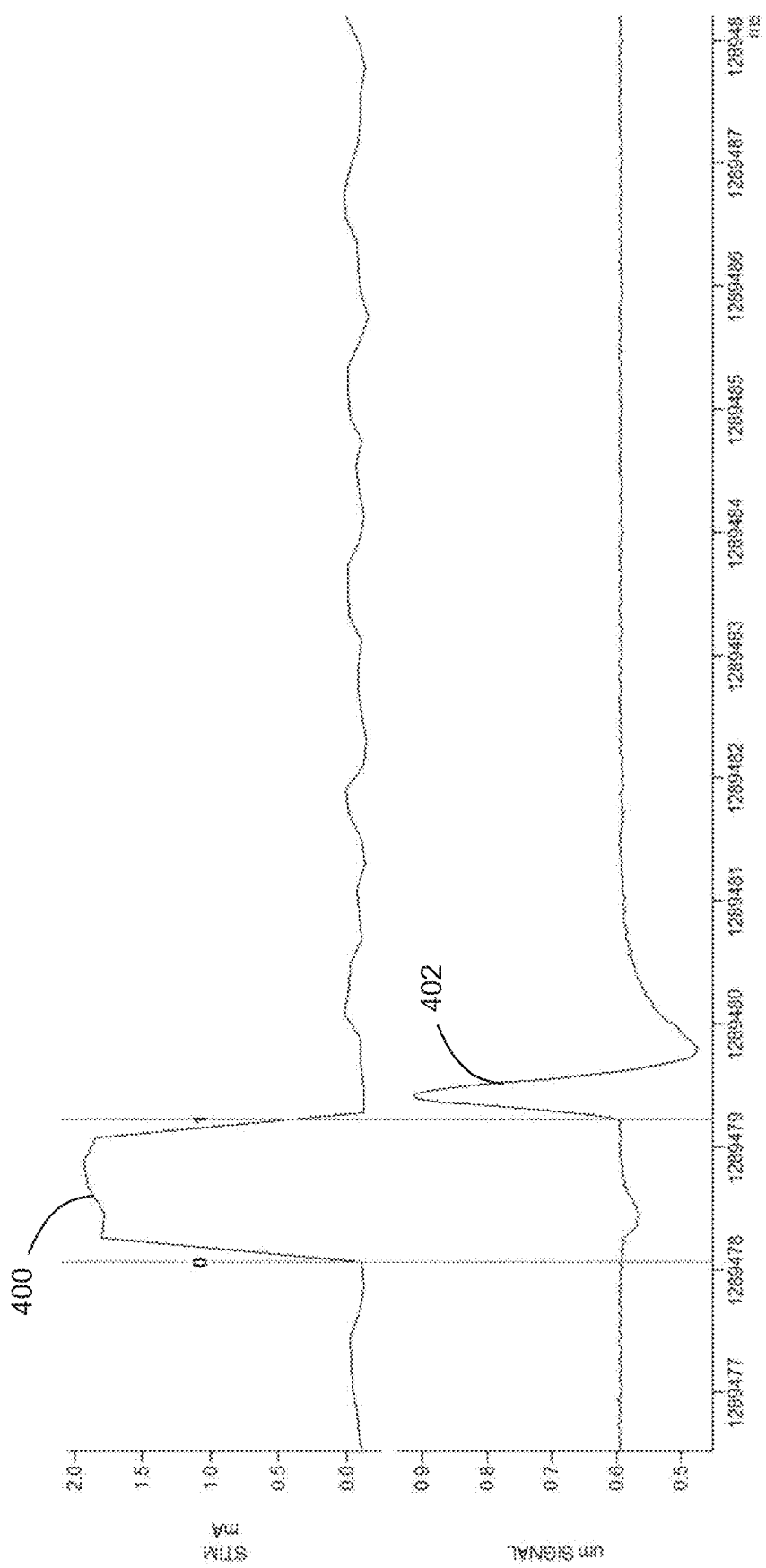
FIG. 4 is an exemplary plot representative of an electrical stimulus and an elicited potential detected in a patient's nervous system.

The ECU 202 can further present information regarding any or all of the applied stimulus, the signal, and the results of any calculations to a user of the system, e.g., via output 218. For example, the ECU 202 can generate a graphical display providing one or more graphs of signal strength vs. time representing the stimulus and/or the received signal. FIG. 4 is an exemplary plot of signal strength vs. time illustrating a stimulus signal 400 and an associated elicited potential 402. Time stamp 0 is indicative of the triggering of the stimulus signal 400 while stamp 1 represents the onset of the elicited potential. In alternative embodiments, the ECU 202 can present information representative of such signals to the user via an audio alert or any other appropriate method of communication.

In some embodiments, the ECU 202 can include a controller 222 in communication with one or both of stimulator 206 and signal processor 210. The controller 222 can be configured to cause stimulator 206 to apply a stimulation signal to the probe 240. Additionally or alternatively, the controller 222 can be configured to analyze signals received and/or output by the signal processor 210. In some embodiments, the controller 222 can act to control the timing of applying the stimulation signal from stimulator 206 and the timing of receiving signals by the signal processor 210.

Exemplary electrical control units have been described. In various embodiments, the ECU 202 can emit stimulus pulses to the probe, receive signals from the probe, perform calculations on the emitted and/or received signals, and present the signals and/or results of such calculations to a user. In some embodiments, the ECU 202 can comprise separate modules for emitting, receiving, calculating, and providing results of calculations. Additionally or alternatively, the functionality of controller 222 can be integrated into the ECU 202 as shown, or can be separate from and in communication with the ECU.

In some embodiments, the ECU 202 can include a switching network configured to interchange which of electrodes 242, 244 of the probe are coupled to which portions of the ECU. For instance, in some examples, the ECU 202 as shown in FIG. 2 can be adjusted so that the stimulator 206 is in electrical communication with electrodes 244 of the probe and the signal processor 210 is in electrical communication with electrodes 242 of the probe. Additionally or alternatively, the ECU 202 includes inputs for receiving connectors electrically coupling the ECU 202 to the electrodes (242, 244) of the probe 240. In some such embodiments, a user can manually switch which inputs receive connections to which electrodes of the probe 240. Such configurability allows for a system operator to adjust the direction of propagation of the elicited potential as desired.

Figure 3:
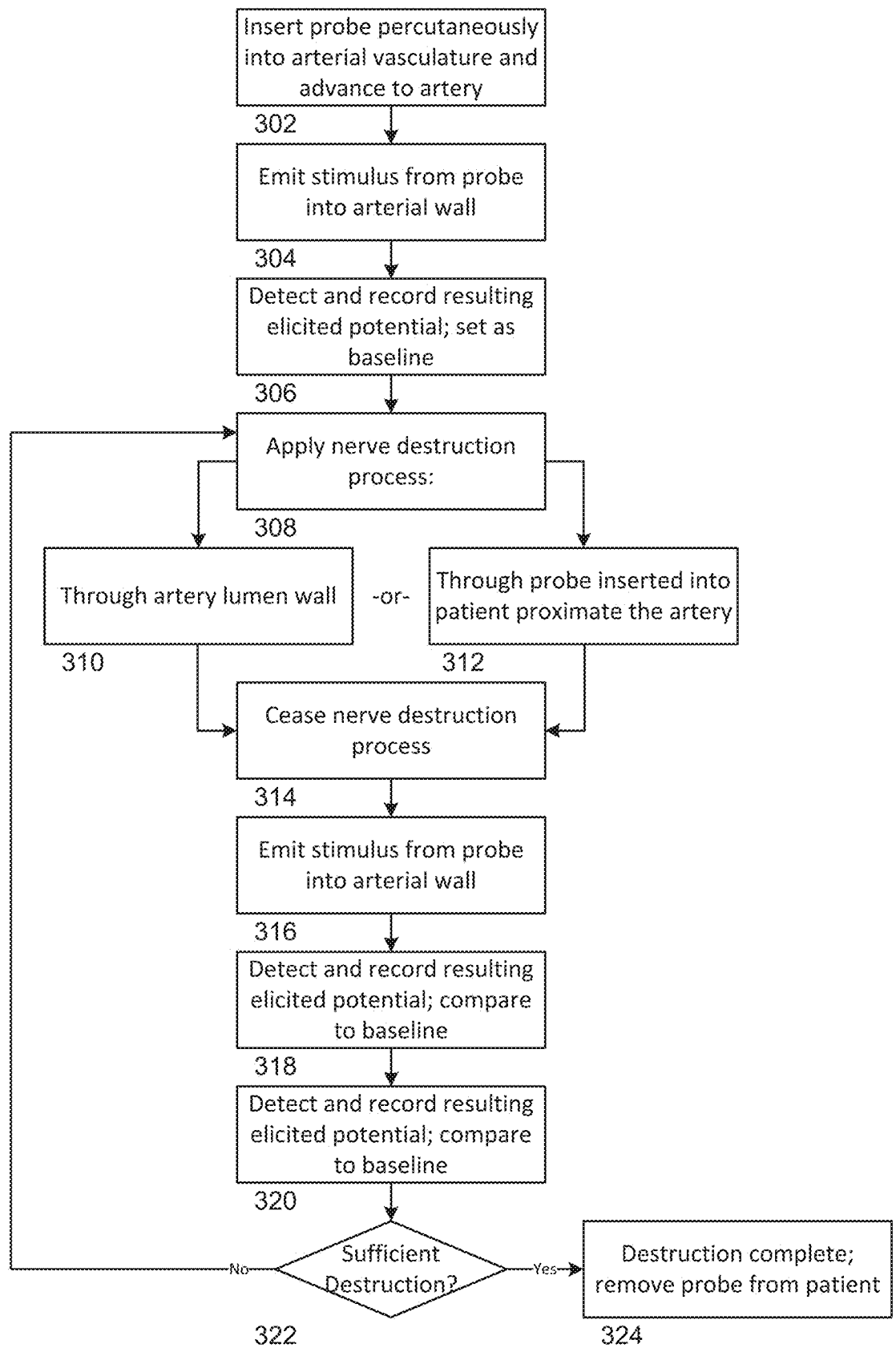
FIG. 3 is a process-flow diagram illustrating an exemplary nerve analysis and destruction process.

Some aspects of the invention include methods of using systems such as those described above. An exemplary method is illustrated in FIG. 3. During use, according to some embodiments, a probe is inserted percutaneously into the arterial vasculature and advanced into an artery (302) such that the electrodes are placed in contact with the arterial lumen wall. Any appropriate probe can be used, such as exemplary probes described above. Additionally, while the method of FIG. 3 is generally directed toward interfacing with an arterial wall, similar methods can be employed in other blood vessels. A stimulus can be emitted into the arterial lumen wall via the probe (304), and the resulting signal (e.g., elicited signal or action potential) can be detected via the probe and recorded to the ECU. Such a measurement can be set as a baseline measurement (306), since no destruction to the nerves has yet been applied. The recorded baseline signal can be stored in a memory in the system.

After recording a baseline measurement, a nerve destruction process can be applied (308) to the nerves within or proximate the artery. Among various embodiments, the nerve destruction means can be applied (i) through the artery lumen wall (310) (e.g., for the purposes of terminating nerve activity) or (ii) through a probe inserted into the patient's abdomen to a position in proximity to the artery (312) (e.g., for the purposes of terminating nerve activity). The destruction process can be ceased (314) after an amount of time, and a stimulus can once again be emitted via the probe (316) and the resulting elicited signal can be detected (318) via the probe.

The detected and recorded elicited signal can be stored in memory and/or compared to the baseline signal (320) previously stored. Based on the comparison, a relative amount of nerve destruction performed by the destructive means can be determined. In some embodiments, the comparison is calculated automatically and a relative amount of destruction is communicated to a user. A user can then determine (322) whether additional destruction is appropriate, or if sufficient destruction has been performed. Alternatively, in some configurations, the determination can be automated. That is, if the controller 222 (as a part of or separate from the ECU 202) can determine whether or not a sufficient amount of destruction has been performed based on an automated comparison. For example, the controller 222 can determine if the comparison satisfies a predetermined condition, the predetermined condition indicating a sufficient amount of destruction has been performed.

Satisfying the predetermined condition can include, in various examples, a reduction of the magnitude of the elicited potential by a predetermined percentage or absolute amount, or a complete elimination of the elicited potential. In such automated embodiments, if it is determined (322) that insufficient destruction has taken place (e.g., the predetermined condition is not met), the controller 222 can cause the destructive means to perform additional destructive processes (308) to the patient's nerves. In other embodiments, a user can manually apply additional destructive processes (308) of insufficient destruction is detected. If sufficient destruction has been performed (e.g., the predetermined condition is met), then the destruction process is complete (324).

In general, this process can be repeated (aside from reacquiring a baseline measurement) until it has been determined that sufficient destruction has been performed. That is, when nerve activity is reduced to an acceptable level. Then, the process is terminated and the probe can be withdrawn from the patient's body (324). FIGS. 5A-5C show the progression of elicited potentials in arterial nerves in response to a stimulus pulse as the relative amount of nerve destruction increases. FIG. 5A is a plot showing a stimulus signal 500a and a detected elicited response 502a before performing a destructive operation on the arterial nerves. In some examples, FIG. 5A can represent a baseline measurement. FIG. 5B illustrates a stimulus signal 500b and a detected elicited response 502b. As can be seen, the elicited response 502b is significantly smaller than elicited baseline response 502a, indicating that significant destruction of arterial nerves has been performed. FIG. 5C illustrates a stimulus signal 500c and a detected elicited response 502c after still more arterial nerve destruction has been performed. As can be seen, the elicited response 502c is much smaller than that of either the elicited baseline response 502a or the response 502b, and is almost non-existent. This implies that further, or possibly complete, arterial nerve destruction has taken place.

During such stimulating, detecting, and destruction procedures, many factors can be considered and/or manipulated to improve system performance. Several factors can be manipulated or taken into account while stimulating nerves to elicit a response, including:

(a) Stimulus Strength—In general, the stimulus must be of a sufficient strength (voltage) to induce an elicited potential. In some embodiments, the stimulus can be of sufficient strength such that most of the nerves along the artery are stimulated. In some situations, such as with the renal artery, many nerves are known to run along the outside of the artery, which may require a stimulus from a probe inside the artery to be sufficiently large for eliciting action potentials in the nerves. In some examples, probes can be configured to provide stimulus signals based on a desired level of current (e.g., in a constant current mode of operation), for example, between approximately 1 mA and approximately 25 mA, while providing whatever voltage is necessary for such currents, in some cases up to or above 100 V. In other examples, stimulations are based only on a desired voltage (e.g., in a constant voltage mode of operation), such as approximately 1 V, or range of voltages, such as between 0.1 V and 1 V, between 1 V and 10 V, etc.

(b) Electrode Separation—In general, for any given voltage, the closer the electrodes are, the stronger the resulting electric field gradient. However, electrodes spaced too close together can result in a short circuit along the tissue itself such that the current is shunted and a voltage gradient is not allowed to develop. In some embodiments, electrodes are separated by approximately 1-3 mm. In some examples, electrode spacing can be designed based on expected action potential magnitude, duration, and/or propagation velocity.

(c) Pulse Width—To elicit such potentials, the pulse often will be applied for a sufficient duration such that the voltage gradient developed by the stimulus pulse has enough time to effect an action (elicited) potential, but not so long as keep the nerves in a constant state of depolarization. In some embodiments, pulse widths can be between 50 to 100 µs; in other systems, pulse widths of approximately 1-10 ms can be used.

(d) Frequency—Finally, the frequency or repetition rate of the stimulus needs to be considered. In some embodiments, a frequency that is too fast can exhaust the nerve while a frequency that is too slow can unnecessarily delay the process. In various embodiments, frequencies within approximately 5-40 Hz can be used.

In addition to considerations of the nerve stimulation pulses, some parameters of the system are configured to maximally elicit bursts of autonomic activity via electrodes placed within the arterial lumen, as well as to enable sufficient detection of autonomic activity. For example, in some embodiments, parameters such as stimulation type, delivery fashion, pulse frequency, pulse duration, phase duration, current intensity, pulse period and pulse train of the electrical stimulation can be selected to have a maximum effect on eliciting autonomic neural activity and be amenable to recording the elicit bursts nearby. In some examples, electrodes can be spaced apart and/or sized according to applied stimulation signals in order to maximize the effect of the applied stimulation. For example, the electrodes can be spaced according to the propagation velocity and/or stimulation pulse width so that the entire duration of a desired pulse shape is used for stimulation purposes between the anode and the cathode.

Further, in some embodiments, various aspects of recording electrodes can be configured to better receive or distinguish elicited potential. For example, in some embodiments, the size of the recording electrodes can be selected based on at least one of the propagation velocity of elicited potentials in the patient's nerves and the pulse width of the elicited potentials. In some embodiments, the recording electrodes have a width that is approximately the same as the pulse width of the elicited potential. In further embodiments, the recording electrodes have a width that is smaller than the pulse width of the elicited potential. In general, a narrow electrode can minimize the amount of noise present at the surface of electrode simultaneously with the elicited potential.

As previously discussed, elicited potentials in autonomic nerves are generally small and are often difficult to detect. Further, the position of autonomic nerves proximate an arterial lumen can make detection of elicited potentials from within the artery difficult. For example, renal artery nerves lie longitudinally along the renal artery and are circumferentially all around the arterial wall as well as outside the renal artery lumen. As such, detection of elicited potentials by an indwelling probe is made difficult both by the barrier presented by the arterial wall itself as well as the distance from the sensing electrodes to the nerves. Thus, it is important to be able to both detect and distinguish such signals from other noise in the patient and system.

One process to enhance the detection of elicited potentials involves expecting any such potentials to be present at a certain time. That is, a known action potential propagation/conduction velocity and electrode spacing allows for creating a temporal window in which the elicited potential can be predicted to arrive at the recording electrode. Accordingly, methods according to the present invention can include receiving elicited signals via the probe within a predetermined time window. For example, with respect to FIGS. 5A-5C, numeral 0 represents the time at which the stimulus potential is applied, while numerals 1 and 2 represent the start and end times in which an elicited potential is expected based on the electrode spacing and the elicited potential propagation velocity. As shown, the detection elicited potentials are generally present within the defined temporal window. Detecting nerve signals within only a predefined temporal window can help prevent the system from receiving noise or other artifacts not associated with elicited potentials and falsely relating them to such potentials.

Additionally or alternatively, various steps can be employed to isolate the detection of elicited potentials from detection of the stimulation signal at the recording electrodes. In general, the stimulation pulse will reach the recording electrodes before the elicited potential arrives. This is because the elicited potential propagates by a different mechanism than the stimulation pulse. While the stimulation pulse propagates toward the recording electrodes due to electrical conduction through body tissues and fluids, elicited potentials propagate along axons via a sequential cell membrane process. Such propagation occurs having a velocity between approximately 0.2 m/s and approximately 200 m/s., which is comparatively slower than the stimulation pulse. Thus, in some instances, the recording electrodes can be blanked for a period of time following the application of the simulation pulse, allowing the stimulation pulse to effectively pass by the recording electrodes without being recorded. Monitoring by the recording electrodes can be resumed after blanking in time to receive the elicited potential following the stimulation pulse.

In some embodiments, the probe can be configured to allow for a maximum separation between the simulating electrode(s) and the recording electrode(s). Such a configuration results in a greater temporal separation of the stimulation pulse and the elicited potential at the recording electrodes when compared to more closely-spaced electrodes. In some examples, the practical distance between the stimulating electrode(s) and the recording electrode(s) is limited by the length of the artery in which the probe is inserted for operation. Thus, in some embodiments, the probe comprises an adjustable distance between the stimulating electrode(s) and the recording electrode(s) in order to allow for the distance between the sets of electrodes to be maximized while allowing the probe to adequately fit within the artery of the patient.

Figure 6:
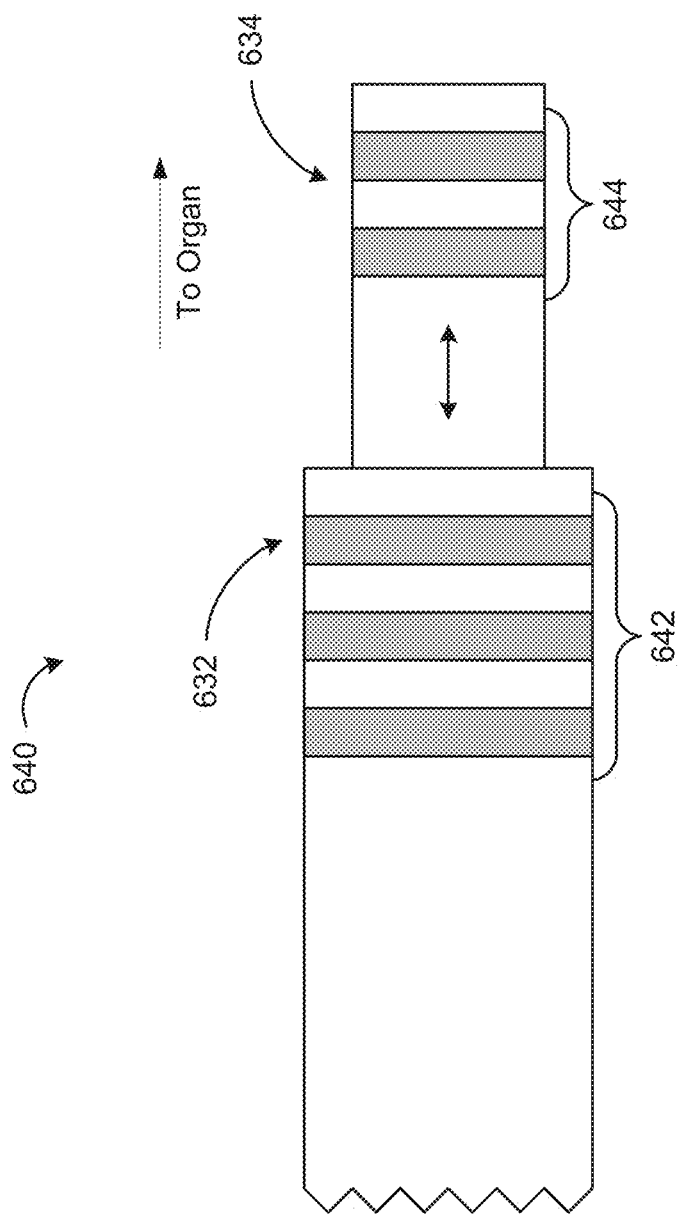
FIG. 6 is an exemplary probe design for inserting into a patient's artery.

FIG. 6 is an exemplary probe configured for adjustable separation of the stimulating and recording electrode(s). As shown, stimulating electrodes 642 are present on a first portion 632 of the probe 640, while recording electrodes 644 are present on a second portion 634 of the probe 640. In the illustrated embodiment, the second portion 634 is located distally from the first portion 632 in a patient's artery, for example, toward an organ. The second portion 634 can be configured to translate relative to first portion 632, allowing for the adjustment of the probe length and the separation between the stimulation 642 and recording 644 electrodes. In some examples, translation of the second portion 634 relative to the first portion 632 is achieved by a telescoping configuration between the first 632 and second 634 portions of the probe 640.

As generally discussed previously, various processing steps can be performed by an ECU or other processor to further distinguish elicited potentials from other signals. As shown in the schematic diagram in FIG. 2, the ECU can include a signal processor comprising an amplifier, filter, and other signal extraction tools. The amplifier can comprise a common-mode rejection amplifier in order to emphasize an elicited signal over the background noise of the artery. In some embodiments, the amplifier comprises a common-mode rejection ratio (CAVA) of approximately 100 dB or more. A band-pass filter can be used to attenuate signals not within an expected frequency band indicative of elicited potentials. Additionally or alternatively, a band-reject filter can be used to specifically attenuate expected noise at an expected frequency. For example, a band-reject filter centered around approximately 60 Hz might be used. Various other signal processing and extraction techniques can similarly be employed, such as the averaging processes herein described.

In some embodiments, various characteristics (e.g., capacitance, resistance, etc.) of components such as the electrodes, circuitry, or parts of the ECU 202, such as an amplifier or filter, can be adjusted either automatically or manually. For example, in some systems, the capacitance of a filter or amplifier can be adjusted to tune bandwidths or resonant frequencies of such components to better extract signals representative of elicited potentials. In some processes, a user or controller 222 can adjust such values and observe the response to such adjustments in order to optimize system operation. That is, in some embodiments, such values are manually adjustable, and a user can adjust such values while observing signal detection performance. In some situations, specific probe types have known properties that affect the stimulation or detection of elicited potentials in the patient. Accordingly, in some embodiments, the ECU 202 can detect or receive a "probe type" input and automatically adjust the capacitance and/or resistance accordingly to allow for enhanced stimulation or amplification and detection of elicited potential. In various embodiments, the "probe type" input can be entered manually, or the system can automatically detect the probe type.

Figure 7:
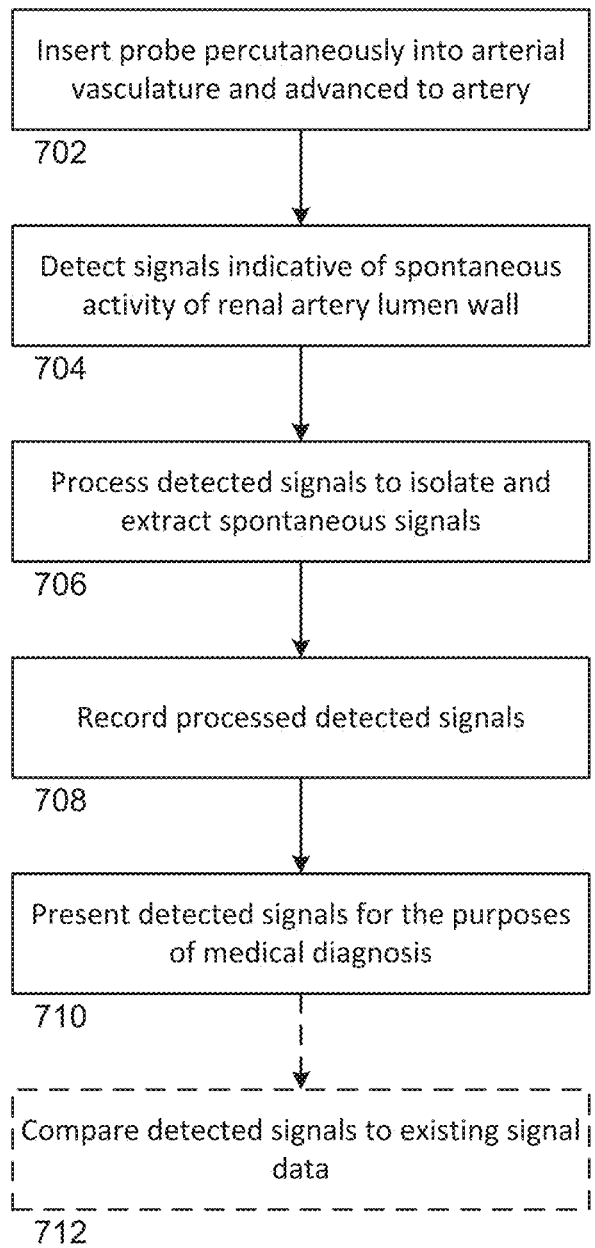
FIG. 7 is a process-flow diagram illustrating an exemplary diagnostic process.

In some embodiments, systems such as those herein described can be utilized for diagnostic purposes. In an exemplary procedure, such as illustrated in FIG. 7, a probe such as those herein described can be inserted into the vasculature of a patient. In various embodiments, the probe is inserted percutaneously, and further can be advanced into an artery (702). The probe can be used to detect signals in the arterial wall indicative of spontaneous or native activity of nerves from within the wall (704), for example, electrical signals. Such detected signals can be processed in order to isolate and extract the desired spontaneous signals (706). Processing can include averaging to eliminate temporal noise, filtering the signal to amplify or to attenuate various frequency bands, or any other processing described herein or otherwise known in the art.

The processed signals can be recorded (708), for example in a temporary or permanent memory, and presented to a user for the purposes of medical diagnosis. Signals can be presented (710), for example, as a plot of signal vs. time on a display. Additionally or alternatively, the signals can be compared to existing signal data (712) for comparing the patient's spontaneous nerve activity to a baseline. In some examples, the patient's spontaneous nerve activity can be compared to that of a healthy patient to assess organ or nervous health. Such a comparison can provide indication as to whether or not ablation may be an effective treatment for the particular patient. In other examples, the spontaneous nervous activity can be analyzed independently from any previously recorded nervous activity to determine the health of the patient's proximate nerves or the viability of nerve treatments on the patient.

Figure 8:
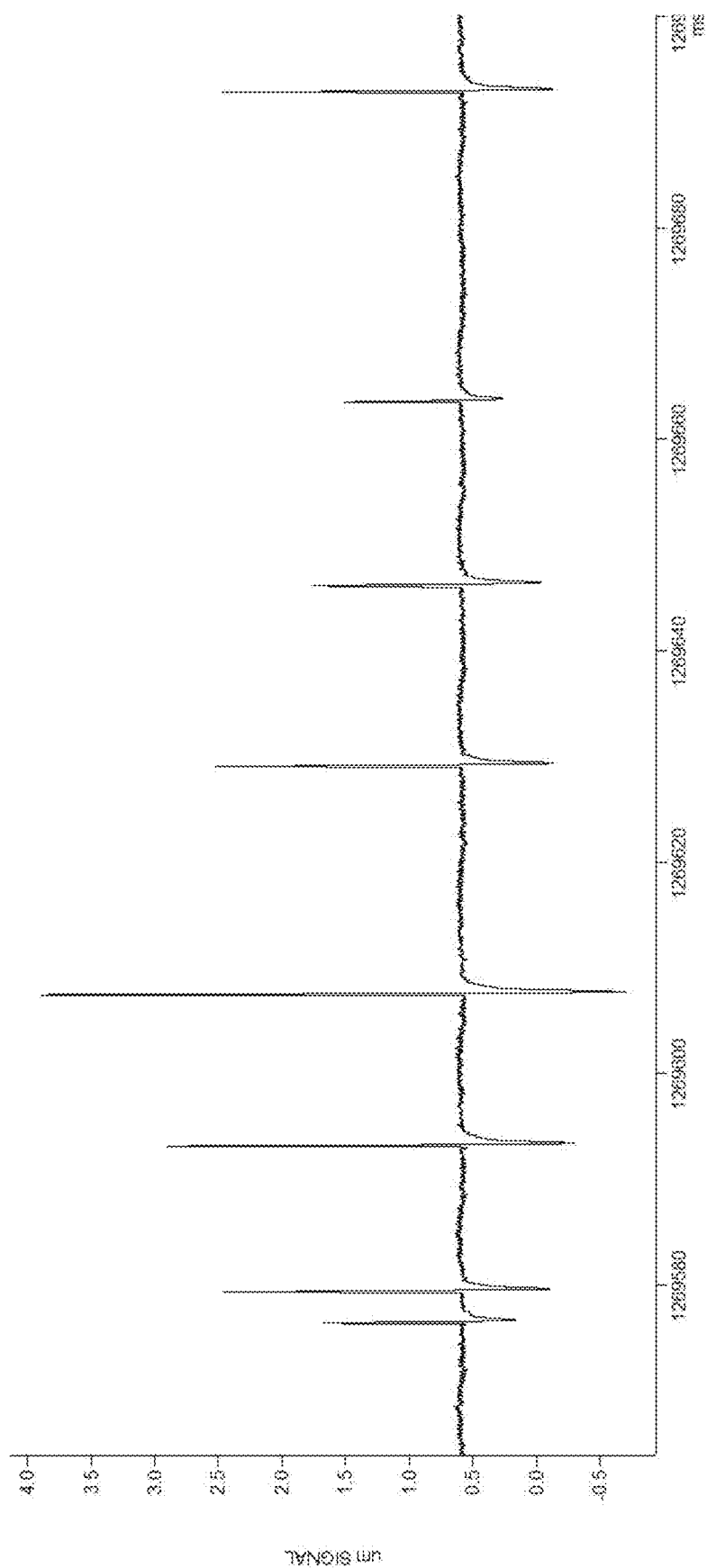
FIG. 8 is an exemplary plot of electrical signals detected in a patient's nervous system.

An exemplary display is shown in FIG. 8, in which the signal is plotted against time, showing extracted spontaneous nerve activity proximate the artery containing the probe. Comparisons between detected nerve activity and a baseline nerve activity stored in memory can provide indications for possible next steps to be performed. For instance, in some examples, if a patient displays little or no spontaneous nerve activity, a clinician may determine that a nerve destruction process is not likely to significantly affect the patient, and may explore alternative treatment options. In other instances, if a patient exhibiting high levels of abnormal nerve activity, a clinician may determine that the patient may benefit from a nerve destruction process. As such, the diagnostic use of the probe recording electrodes can allow for the execution of an informed treatment plan rather than the arbitrary destruction of nerve function. Subsequently, if nerve destruction is desired, operations such as those described above, for example as in FIG. 3, can be carried out using the system.

Various examples of systems and methods have been described. The description provided herein is exemplary in nature and is not intended to limit the scope, applicability, or configuration of the invention in any way. Rather, the description provides practical illustrations for implementing various exemplary embodiments. Examples of constructions, materials, dimensions, and manufacturing processes are provided for selected elements, and all other elements employ that which is known to those of skill in the field. Those skilled in the art will recognize that many of the examples provided have suitable alternatives that can be utilized. These and others are within the scope of the following claims.

The invention claimed is:

1. A system for intravascular assessment of neural activity, the system comprising:
 a probe configured to be temporarily inserted into a blood vessel of a patient;
 a recording electrode located on the probe and capable of detecting a neural electrical signal via an interior wall of the blood vessel when the probe is temporarily inserted into the blood vessel such that the recording electrode is located in the blood vessel against the interior wall of the blood vessel; and
 electronic circuitry in electrical communication with the recording electrode and configured to:
  receive the neural electrical signal from the recording electrode;
  control adjustment of a capacitance value of a variable capacitance in the system to affect the received neural electrical signal; and
  output the affected neural electrical signal.

2. The system of claim 1, further comprising a stimulating electrode to transmit an electrical stimulus via the interior wall of the blood vessel proximate a nerve, and wherein the electronic circuitry is configured to provide an electrical stimulation signal to the stimulating electrode to evoke a response neural action potential in the nerve.

3. The system of claim 2, wherein the system is configured to ablate nerve tissue of a patient.

4. The system of claim 3 further comprising:
 a memory for storing one or more output signals, wherein the electronic circuitry is configured to compare a first output signal representative of a neural electrical signal received at a first time to a second output signal stored in memory, the second output signal being representative of a neural electrical signal received at a second time, the second time being earlier than the first time; and
 wherein the electronic circuitry is configured to determine, from the comparison, a difference in nerve activity proximate the blood vessel.

5. The system of claim 4, wherein to determine the difference in nerve activity comprises determining a relative amount of nerve destruction performed.

6. The system of claim 5, wherein the electronic circuitry is configured to:
 (i) provide a first electrical signal to the stimulation electrode;
 (ii) produce a first output signal representative of a received first responsive neural electrical signal;
 (iii) apply a nerve destruction process;
 (iv) provide a second electrical signal to the stimulation electrode;
 (v) produce a second output signal representative of a received second responsive neural electrical signal;
 (vi) compare the second output signal to an output signal representative of a neural electrical signal received before the application of the nerve destruction process of step (iii); and
 (vii) repeat steps (iii)-(vi) until the comparison meets a predetermined condition.

7. The system of claim 5, wherein the electronic circuitry is configured to determine an effect of the nerve destruction based on an elicited neural action potential correlative to the difference in nerve activity.

8. The system of claim 2, wherein the stimulating electrode and the recording electrode each comprise one or more electrodes.

9. The system of claim 8, in which the one or more electrodes comprise one or more ring electrodes.

10. The system of claim 8, in which the one or more electrodes comprise one or more electrodes providing a 360 degree circumferential contiguously electrically conductive electrode.

11. The system of claim 2, wherein the stimulating electrode comprises an anode and a cathode and the recording electrode comprises an active electrode and a reference electrode.

12. The system of claim 11, wherein the anode and the cathode of the stimulating electrode are separated by 1-3 millimeters.

13. The system of claim 2, wherein the electronic circuitry comprises a receiving portion configured to receive the neural electrical signal from the recording electrode, and wherein the electronic circuitry is configured to adjust an electrical impedance of the receiving portion.

14. The system of claim 2, wherein to adjust the capacitance value includes adjusting the capacitance value for tuning a bandwidth or a frequency characteristic of the electronic circuitry to extract the received neural electrical signal to be representative of the evoked neural action potential.

15. The system of claim 2, wherein the electronic circuitry is configured to apply a blocking electrical signal to the blood vessel to inhibit propagation of the neural electrical signal in the nerve.

16. The system of claim 1, wherein to adjust a capacitance value includes to automatically adjust the capacitance value based on received probe type information.

17. The system of claim 16, wherein the probe type information includes a property of the probe on which the recording electrode is included.

18. The system of claim 17, wherein the probe comprises a bipolar stimulating electrode that includes an anode and a cathode separated by a specified distance.

19. The system of claim 17, wherein the probe comprises first and second electrodes in the form of an active and inactive pair.

20. The system of claim 1, wherein the electronic circuitry includes an amplifier with capacitance control coupled to the recording electrode, and wherein the electronic circuitry is configured to adjust a capacitance value of a variable capacitance of the capacitance control in the system to affect the received neural electrical signal.

21. The system of claim 20, in which the capacitance control provides impedance loading prior to the amplifier.

22. The system of claim 20, in which the capacitance control provides impedance loading incorporated into the amplifier.

23. The system of claim 22, in which the capacitance control is configured to change a resonant frequency or other amplifier property of the amplifier.

24. The system of claim 1, wherein the electronic circuitry includes a common-mode rejection ratio of at least 100 dB.

25. The system of claim 1, wherein the electronic circuitry is further configured to:
    present information including at least one of: the output signal, a characteristic of the received neural electrical signal, a processing step performed in the processing of the affected electrical signal, or a result of the processing step.

26. The system of claim 1, wherein the capacitance value is configured to be adjusted to enable detection of a non-elicited intrinsic neural action potential in a nerve, and wherein the capacitance value is user-adjustable.

27. The system of claim 1, in which the electronic circuitry is configured to adjust a capacitance value of a variable capacitance in the system to affect the received neural electrical signal, including adjusting at least one of an impedance, a separation distance, a size, or a geometry of one or more intravascular recording electrodes.

28. The system of claim 1, wherein the electronic circuitry includes an amplifier with capacitance control coupled to the recording electrode, and wherein the electronic circuitry is configured to adjust a capacitance value of a variable capacitance of the capacitance control in the system to affect the received neural electrical signal.

29. The system of claim 1, in which the electronic circuitry is configured to adjust a capacitance value of a variable capacitance in the system to affect the received neural electrical signal, including adjusting the capacitance value of a variable capacitance in the system to accommodate at least one of an impedance, a separation distance, a size, or a geometry of one or more intravascular recording electrodes.

* * * * *